United States Patent [19]

Barcel

[11] Patent Number: 5,228,455
[45] Date of Patent: Jul. 20, 1993

[54] IMPLANT TOOL FOR EXTENDABLE/RETRACTABLE POSITIVE FIXATION LEAD

[75] Inventor: James E. Barcel, Simi Valley, Calif.

[73] Assignee: Siemens Pacesetter, Inc., Sylmar, Calif.

[21] Appl. No.: 703,222

[22] Filed: May 20, 1991

[51] Int. Cl.$^5$ .............................................. A61N 1/05
[52] U.S. Cl. ..................................... 128/785; 128/642
[58] Field of Search ............................... 128/784–786, 128/642, 790, 419 P

[56] References Cited

U.S. PATENT DOCUMENTS

| | | | |
|---|---|---|---|
| 4,209,019 | 6/1980 | Dutcher et al. | 128/784 X |
| 4,217,913 | 8/1980 | Dutcher | 128/785 |
| 4,253,462 | 3/1981 | Dutcher et al. | 128/784 X |
| 4,452,254 | 6/1984 | Goldberg et al. | 128/785 |
| 4,463,765 | 8/1984 | Gold | 128/785 |
| 4,475,560 | 10/1984 | Tarjan et al. | 128/785 |
| 4,570,642 | 2/1986 | Kane et al. | 128/785 |
| 4,649,938 | 3/1987 | McArthur | 128/785 |
| 4,923,371 | 6/1990 | Malis et al. | 128/642 |
| 5,003,992 | 4/1991 | Holleman et al. | 128/785 |
| 5,020,545 | 6/1991 | Soukup | 128/785 |
| 5,076,285 | 12/1991 | Hess et al. | 128/785 X |
| 5,129,404 | 6/1992 | Spehr et al. | 128/785 |
| 5,152,299 | 10/1992 | Soukup | 128/785 |

OTHER PUBLICATIONS

Furman, et al.; *A Practice of Cardiac Pacing*, Chapter 5 (Holmes, David R. Jr., "Permanent Pacemaker Implantation"), pp. 97–127 (Futura Publishing Co., Mt. Kisko, N.Y. (1986).

Calfee, et al., "A Voluntary Standard for 3.2 mm Unipolar and Bipolar Pacemaker Leads and Connectors", *Pace*, 9:1181–85 (Nov.–Dec. 1986, Part II).

*Primary Examiner*—Lee S. Cohen
*Assistant Examiner*—Jeffrey R. Jastrzab
*Attorney, Agent, or Firm*—Bryant H. Gold; Lisa P. Weinberg

[57] ABSTRACT

An implant tool for use with an endocardial or other implantable lead having an extendable/retractable positive fixation tip includes a hollow cylindrical housing and a custom designed stylet. The cylindrical housing attaches to a proximal end of the implantable lead. The stylet is inserted through the implant tool and into a lumen of the lead. The presence of the stylet, made from a length of relatively stiff wire, helps guide the distal tip of the lead to a desired implant location. The cylindrical housing includes a body portion and an end portion. The end portion is rotatable relative to the body portion. The stylet includes a knob on its proximal end, and also includes a stub pin slightly forward of its proximal end. The stub pin is received within a slot along the side of the cylindrical housing. Two spaced-apart recesses along the length of the slot allow the stub pin to be respectively held therein. When the stub pin is held in a first recess, the stylet wire has advanced sufficiently far into the lead to facilitate implantation of the lead, but retains the positive fixation tip in its retracted position. When the stub pin is locked in a second recess, the stylet wire has advanced sufficiently far into the lead to engage the positive fixation tip and move it to its extended position. A method of using the implant tool is also disclosed.

12 Claims, 3 Drawing Sheets

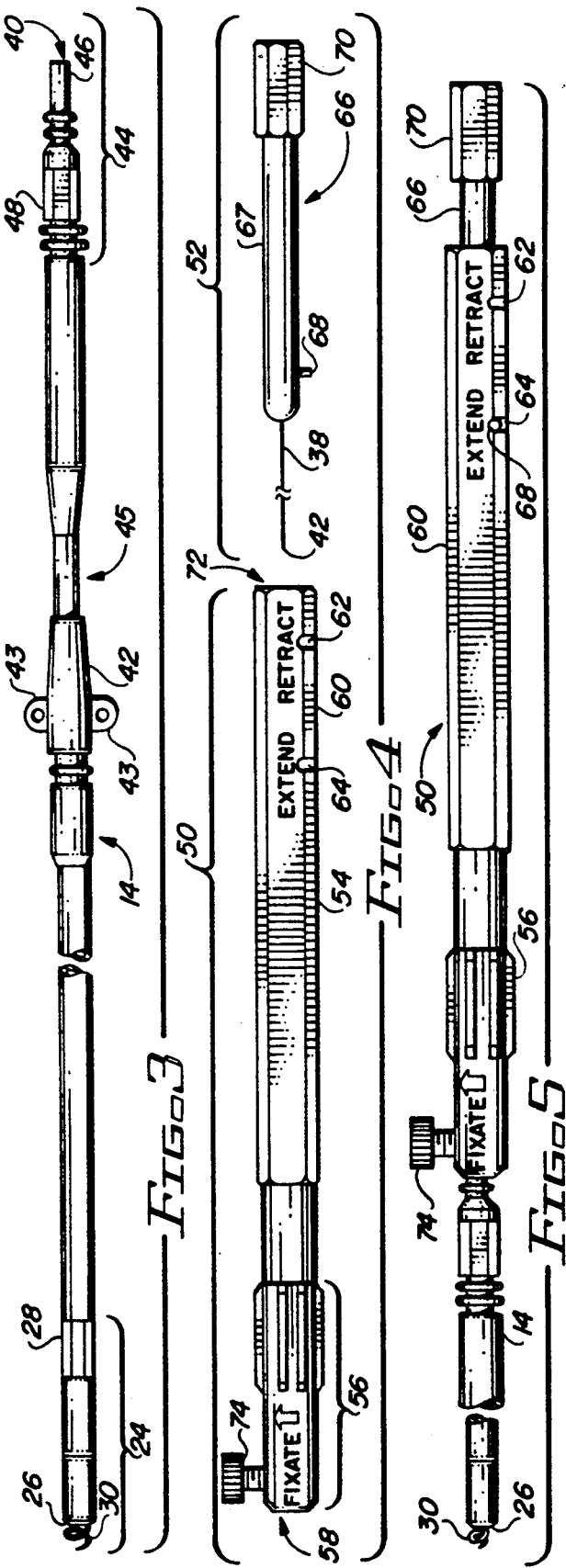

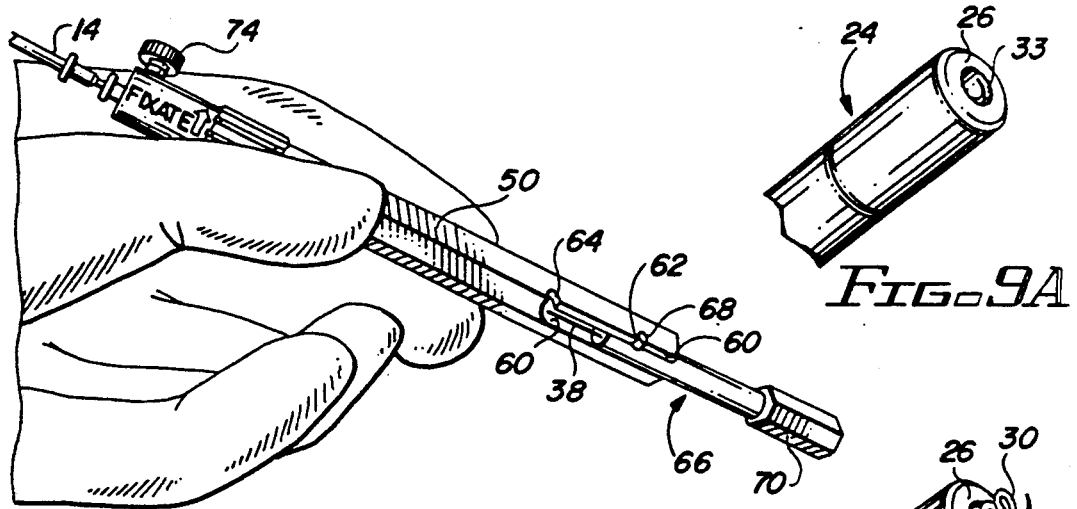
FIG. 9
FIG. 9A
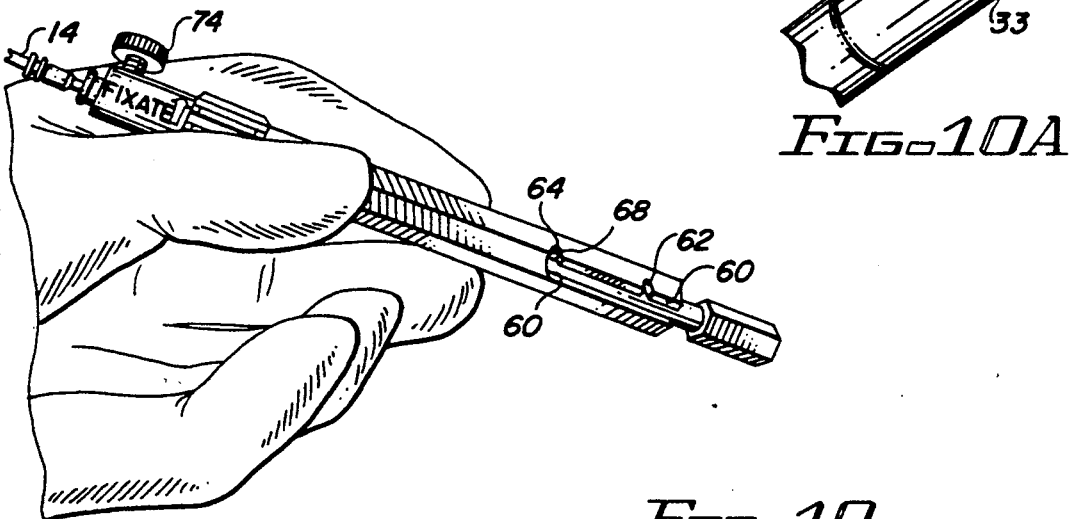
FIG. 10
FIG. 10A
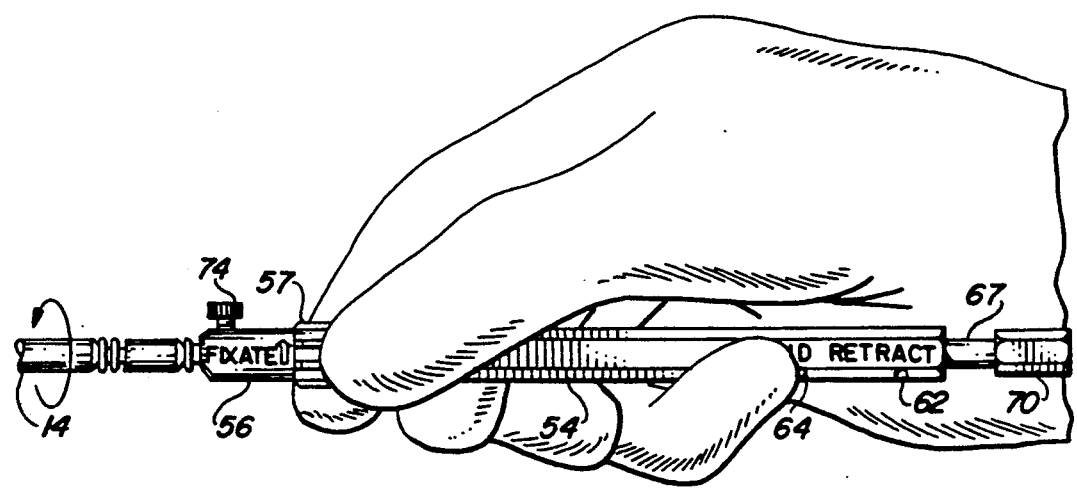
FIG. 11

IMPLANT TOOL FOR EXTENDABLE/RETRACTABLE POSITIVE FIXATION LEAD

BACKGROUND OF THE INVENTION

The present invention relates to an implant tool for implanting a tissue-stimulating lead having an extendable/retractable positive fixation tip, such as an endocardial lead having an extendable/retractable screw-in (helix) tip.

A tissue-stimulating lead is used with a tissue-stimulating device, such as an implantable pacemaker, in order to electrically couple the stimulating device to a desired tissue location. When the stimulating device is a cardiac pacemaker, for example, the tissue-stimulating lead, also referred to as a "pacing lead," connects the pacemaker's electrical circuits directly with a desired chamber of the heart. Access to the heart is usually achieved transvenously, i.e., the lead is inserted into the heart through a major vein, such as the superior vena cava, thereby avoiding the trauma of open heart surgery. One or more electrodes at or near the end of the lead placed inside of the heart—referred to as the "distal end"—contact the cardiac tissue therein at the desired location. The electrode(s) are electrically connected via insulated conductors within the lead to an appropriate connector at the other end of the lead—referred to as the "proximal end." Herein, the terms "distal" and "proximal" are used to describe the ends of a lead, or tools or components or other elements used with a lead, that are respectively farthest or closest to a medical device to which the lead is, or will be, attached.

After an implantable lead is transvenously or otherwise implanted, and after various electrical tests have been made to confirm that the lead electrode(s) is positioned at the proper tissue location, the connector at the proximal end of the lead is detachably inserted into an appropriate mating connector of a medical device, such as a pacemaker, thereby electrically coupling the desired tissue location to the electrical circuits within the medical device.

The distal tip of the implantable lead is held at a desired tissue location by either positive fixation or passive fixation. Positive fixation (sometimes called "active fixation") involves the use of some type of mechanism or means for actively securing and holding the body tissue in contact with the distal tip. The most common type of positive fixation is achieved using a screw-in helix tip located at the distal end of the lead. Positive fixation is achieved by literally screwing the helix tip into the tissue. In contrast, passive fixation involves temporarily holding the distal tip near the desired location, e.g., through the use of tines near the distal electrode that become entangled with trabeculae located inside the heart, until some sort of tissue ingrowth can occur into the lead tip in order to firmly hold it in its desired position.

The advantages of positive fixation leads are well known in the art. A much more reliable tissue contact can be made and maintained using a positive fixation lead than can be made using a passive fixation lead. Such contact can be established immediately without having to wait for tissue ingrowth. Further, a positive fixation lead that has been properly affixed to body tissue is not easily dislodged in the event the patient is bumped, or suffers some other type of physical shock.

A common technique used to implant a positive fixation lead is to insert the lead transvenously into the desired tissue contact location, e.g., inside of the heart. However, such transvenous insertion requires that the positive fixation tip be maintained in a retracted position until the distal tip of the lead is at the desired tissue contact location. Otherwise, during the process of inserting the lead, the positive fixation tip, comprising, e.g., a sharp, protruding screw-in helix tip, could easily become entangled with and/or damage delicate body tissue at a location other than the desired tissue contact location. Thus, it is known in the art to use positive fixation leads having extendable/retractable helix tips. A simple construction of such a lead incorporates a sliding carrier that is inserted into a tip housing at the distal end of the lead. A screw-in helix tip is attached to the distal end of the carrier. Prior to placement of the lead, the carrier is axially pushed, from the distal end of the lead, to a retracted position such that the screw-in tip does not protrude from the distal end. Once the lead has been positioned for placement, the screw-in tip is extended by axially pushing the carrier, from the proximal end of the lead through the use of a stylet, to an extended position.

U.S. Pat. No. 4,649,938, issued to McArthur, shows a variation of this basic extendable/retractable construction that uses internal biasing means, e.g., a coiled spring, to maintain the carrier in its retracted position. Further, McArthur teaches the use of an O-ring to seal the carrier as it axially moves from its retracted position to its extended position. The O-ring rolls as the carrier moves, thereby facilitating low friction movement. An axial force must be applied to the stylet as the screw-in tip is screwed into body tissue. Once positive fixation has occurred, the internal biasing means tends to pull the tissue in contact with the electrode, thereby helping maintain a good tissue-electrode interface.

When a positive fixation tip is extended to its protruding position through the use of a stylet, it is necessary to apply and maintain an axial force to the stylet in order to keep the tip in its extended position. Otherwise, the body tissue contacting the tip tends to push the tip back into its retracted position. This axial force must continue to be applied as the positive fixation tip is affixed to the body tissue, e.g., realized by rotating the lead when the positive fixation tip is a screw-in helix tip. If too little axial force is applied, the tip may not remain fully extended, and may therefore not fully engage the body tissue. What is needed, therefore, is a convenient means of applying the correct axial force to a stylet in order to assure that the extendable/retractable tip is fully extended during the fixation process.

Even if the correct axial force is applied to the stylet in order to fully extend the positive fixation tip, this axial force must continue to be applied while the lead is rotated, or other action is undertaken to positively engage the tip with the body tissue. Heretofore, this has been at least a two-handed operation, applying the axial force to the stylet with one hand, while rotating the lead (or stylet, in some types of leads) with the other hand. Needless to say, such two-handed operation is cumbersome and difficult to do while maintaining the proper axial force on the stylet. There is thus a need in the art for an implant tool that facilitates the application of the proper axial force on the stylet while allowing the helix tip to be rotated the proper number of turns to assure proper fixation to body tissue. Preferably, such an implant tool would also be usable with one hand, thereby allowing the implant physician, or other medical personnel, to use his or her other hand for other important activities that must occur during the implant operation.

SUMMARY OF THE INVENTION

The present invention addresses the above and other needs by providing an implant tool and method that selectively maintains the correct stylet position to keep an extendable/retractable positive fixation tip retracted, applies the correct axial force to extend the tip, and allows one-handed rotation of the tip while maintaining it in its extended position. As with leads having extendable/retractable positive fixation tips of the prior art, movement of a positive fixation tip of an implantable lead from a normally retracted position to an extended position in accordance with the present invention is actuated by inserting a stylet through the lead until a distal tip of the stylet engages the positive fixation tip. Once extended, the positive fixation tip, which typically comprises a sharp wire wound in the shape of a helix, is positively secured to body tissue by rotating the lead, thereby screwing the helix tip into the body tissue. Unlike the prior art, however, the implant tool of the present invention advantageously facilitates this implant process by holding and maintaining the stylet in one of two positions. In a first position, the stylet has advanced sufficiently far within the lead to allow the lead to be implanted and guided to a desired implant location, but not sufficiently far so as to move the positive fixation tip to its extended position. In a second position, the stylet has advanced sufficiently far within the lead to move the positive fixation tip to its extended position and maintains this position with a constant axial force. Further, the tool facilitates one-handed rotation of the lead, and thereby fixation of the tip to body tissue, once the desired implant location has been reached and the tip has been extended.

The implant tool includes a hollow cylindrical housing and a specially designed stylet. A proximal end of the implantable lead is detachably secured to one end of the cylindrical housing. The stylet, comprising a length of relatively stiff yet flexible wire, is inserted through the implant tool and into a lumen of the lead. The stylet is made from a length of wire and includes a knob on its proximal end, which knob facilitates rotation of the stylet relative to the cylindrical housing. The stylet includes a stub pin slightly forward of its proximal end. The stub pin protrudes out from the stylet wire and is adapted to be received within a slot along the side of the cylindrical housing once the stylet has been inserted through the implant tool sufficiently far to engage the stub pin. Two spaced-apart recesses along the length of the slot allow the stub pin to be locked therein by rotating the stylet when the stub pin is adjacent the desired recess. When the stub pin is locked in a first recess, the stylet wire has advanced sufficiently far into the lead to allow the lead to be implanted, but has not engaged the positive fixation tip so as to move the tip to its extended position. When the stub pin is locked in a second recess, the stylet wire has advanced sufficiently far into the lead to engage the positive fixation tip and move it fully to its extended position.

Thus, in accordance with one aspect of the invention, the implant tool selectively holds the stylet in a first position, wherein the positive fixation tip is retracted, or a second position, wherein the positive fixation tip is extended. Hence, when inserting the lead, e.g., transvenously, to its desired implant location, the stylet is conveniently locked in its first position, thereby keeping the tip in its retracted position. Once the desired implant location has been attained, the stylet is readily changed to its second position, thereby allowing positive fixation to occur.

In accordance with another aspect of the invention, the cylindrical housing includes a body portion and an end portion. The end portion is rotatable relative to the body portion. The proximal end of the lead is detachably secured to the rotatable end portion during implant. Thus, once the desired implant location has been reached, the implant tool may be conveniently held in one hand while rotating the rotatable end portion between thumb and finger(s) of the hand, thereby also rotating the lead and providing a convenient means for positively attaching the fixation tip of the lead to body tissue.

One embodiment of the present invention may thus be characterized as an implant tool for use with an implantable lead. The implantable lead used with such an implant tool has a lead body intermediate a proximal end and a distal end, an extendable/retractable positive fixation tip at its distal end, and a connector pin at its proximal end. The connector pin and lead body have a lumen through their centers through which a stylet may be inserted. When the stylet has been inserted sufficiently far within the lead, a distal tip of the stylet engages the extendable/retractable positive fixation tip, which is normally held in a retracted position, and pushes it towards its extended position.

The implant tool in accordance with this characterization of the invention includes a hollow cylindrical housing adapted for being held in one hand. At the distal end of the cylindrical housing locking means are provided for detachably connecting the connector pin of the implantable lead thereto. The stylet is inserted into the implant tool at the proximal end of the cylindrical housing and is longitudinally guided therethrough to the lumen of the connector pin and lead. In this manner, the stylet may be inserted through the housing into the lead body. The cylindrical housing includes stylet holding means for selectively holding the stylet in a tip retracted position or a tip extended position. The tip retracted position comprises a position whereat the stylet has not advanced sufficiently far through the lead body to push the fixation tip of the endocardial lead to its extended position. The tip extended position comprises a position whereat the stylet has advanced sufficiently far through the lead body to push the fixation tip of the endocardial lead to its extended position. Thus, the implant tool provides a convenient means for maintaining the fixation tip in its retracted position by holding the stylet in the tip retracted position, or for maintaining the fixation tip in its extended position by moving the stylet to the tip extended position.

Another embodiment of the invention may be characterized as a stylet for use with an implant tool and an implantable lead, the implant tool and implantable lead being substantially as described above. The stylet comprises a length of relatively stiff wire having a distal tip and a proximal end, the distal tip of the wire being adapted to be inserted through the lumen of the lead to help guide the placement of the lead during implantation. The distal tip of the wire is further adapted to engage the extendable/retractable positive fixation tip of the lead and push this fixation tip towards an extended position, from which extended position the fixation tip may be positively engaged with body tissue.

The stylet includes a stub pin or tab affixed to the wire near its proximal end. This stub pin protrudes out from the wire a short distance, and is adapted for selective engagement with holding means within the implant tool for holding the wire relative to the implant tool in one of two holding positions. A first holding position maintains the distal tip of the wire short of engagement with extendable/retractable positive fixation tip. A second holding position places the distal tip of the wire in engagement with said extendable/retractable positive fixation tip so as to push the fixation tip to its extended position.

Still a further embodiment of the invention may be characterized as apparatus for implanting an implantable lead. Such implant apparatus includes: (a) an implantable lead, substantially as described above; (b) a stylet, also substantially as described above; and (c) holding means for holding the stylet within a lumen of the lead from a location at the proximal end of the lead in one of two holding positions. A first holding position of the holding means maintains the distal tip of the stylet short of engagement with an extendable/retractable positive fixation tip of the lead. A second holding position places the distal tip of the stylet in engagement with the extendable/retractable positive fixation tip and causes the positive fixation tip to assume its extended position. Advantageously, by using such implant apparatus, the positive fixation tip may be maintained in its retracted position during implantation of the lead by simply maintaining the stylet in the first holding position. Further, once the lead has been implanted, the positive fixation tip may be extended to its extended position by merely placing the stylet in the second holding position, thereby allowing positive engagement of the tip with body tissue. Additionally, it should be noted that the present invention includes a method of implanting an implantable lead, e.g., an endocardial lead, having an extendable/retractable positive fixation tip. Such lead has a proximal connector pin adapted for being connected to a medical device, such as a pacemaker. Further, the connector pin and lead have a lumen through the center thereof through which a stylet may be inserted. Moreover, the lead typically includes biasing means at its distal tip for tending to pull the extendable/retractable positive fixation tip into a retracted position. The positive fixation tip is physically coupled to the lead such that rotation of the lead rotates the positive fixation tip. The implant method includes the steps of:

(a) Detachably connecting the proximal connector pin of the lead to a distal end of a hollow implant tool. This distal first end is preferably rotatable relative to a body of the implant tool.

(b) Inserting the stylet axially through the implant tool and into the lumen of the lead a first prescribed distance. This first prescribed distance is determined by the location of a mark or tab on the stylet relative to at least one mark on the body of the implant tool. This first prescribed distance is selected to assure that a tip of the stylet has not advanced sufficiently far within the lead to push the positive fixation tip of the lead to an extended position.

(c) Locking the stylet within the implant tool and the lead at the first prescribed distance while transvenously inserting the lead into a patient until the fixation tip (which is in its retracted position) is at a desired implant location.

(d) Further inserting the stylet axially through the implant tool and the lead a second prescribed distance. This second prescribed distance is determined by the location of the mark on the stylet relative to the at least one mark on the body of the implant tool. This second prescribed distance is selected such that a tip of the stylet has advanced sufficiently far within the lead to push the positive fixation tip to its extended position.

(e) Locking the stylet within the implant tool and the lead at the second prescribed distance while rotating the lead, e.g., by rotating the distal end of the implant tool relative to the body of the implant tool and stylet. This action causes the positive fixation tip to also rotate, thereby positively securing the tip to body tissue at the desired implant location.

(f) Removing the stylet from the lead and implant tool.

(g) Detaching the connector pin from the first end of the implant tool.

It is thus a feature of the present invention to provide an implant tool, and method of using the same, that facilitates the fixation of a extendable/retractable positive fixation tip to body tissue.

It is another feature of the invention to provide such an implant tool and method that selectively yet positively locks a stylet in one of two positions, a first position allowing the positive fixation tip to be maintained in a retracted position; and a second position forcing the positive fixation tip to an extended position and maintaining it in this extended position with a constant axial force.

It is an additional feature of the invention to provide such an implant tool that provides a visual indication as to the position in which the stylet is locked.

It is yet another feature of the invention to provide such an implant tool that can be conveniently held in one hand while rotating the lead using the thumb and fingers of the same hand, which lead rotation effectuates the positive fixation of the extended positive fixation tip.

BRIEF DESCRIPTION OF THE DRAWINGS

The above and other aspects, features and advantages of the present invention will be more apparent from the following more particular description thereof, presented in conjunction with the following drawings, wherein:

FIG. 1 shows a common technique for transvenously implanting an endocardial lead;

FIG. 2 is an end view, partially broken away, of a bipolar implantable lead having an active fixation distal tip, showing the active fixation tip in its extended position;

FIG. 3 is a plan view of a bipolar implantable lead having an active fixation distal tip;

FIG. 4 shows a fixation tool and stylet made in accordance with the present invention;

FIG. 5 shows the fixation tool and stylet of FIG. 4 as used with the implantable lead of FIG. 3;

FIG. 9 shows the implant tool of FIG. 4 with the lead attached thereto and with the stylet locked in a "retract" position of the implant tool;

FIG. 9A shows an inset of the tip of the lead with the stylet of FIG. 9 locked in the retract position;

FIG. 10 shows the implant tool of FIG. 4 with the lead attached thereto and with the stylet locked in an "extend" position of the implant tool;

FIG. 10A shows an inset of the tip of the lead with the stylet of FIG. 10 locked in the extend position; and FIG. 11 illustrates the one-hand technique of rotating the implantable lead using the implant tool of the present invention.

Corresponding reference characters indicate corresponding components throughout the several views of the drawings.

DETAILED DESCRIPTION OF THE INVENTION

Figure 6:
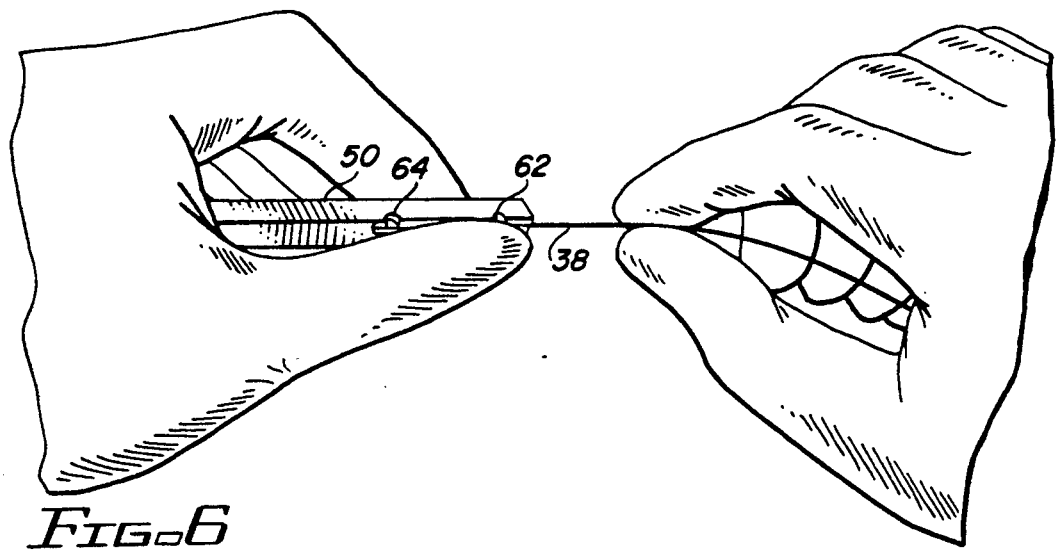
FIGS. 6–7 illustrate different techniques of inserting the stylet of FIG. 4 through the fixation tool and implantable lead.

The following description is of the best mode presently contemplated for carrying out the invention. This description is not to be taken in a limiting sense, but is made merely for the purpose of describing the general principles of the invention. The scope of the invention should be determined with reference to the claims.

Before describing the present invention in detail, it will first be helpful to briefly review the manner in which an implantable lead is normally implanted within a patient. Such review will not only help point out the advantages of using a lead having an extendable/retractable positive fixation tip, but will also help highlight the need for the present invention.

Reference is thus made to FIG. 1 where there is shown a common technique for transvenously implanting an endocardial lead 14 within the heart 18 of a patient 16. A subclavian vein 20 is entered at a desired puncture point 22. The lead 14 is inserted through the puncture point until a distal tip 24 of the lead is at a desired tissue contact location within the heart. While this tissue contact location is shown as being near the apex of the ventricle in FIG. 1, it is to be understood that this is only exemplary and that there are numerous possible tissue contact locations within the heart, both within the ventricle and the atrium. The proximal end of the lead 14, not shown in FIG. 1, is then routed to a desired location for connection with an appropriate medical device, e.g., a pacemaker. Normally, the medical device is also implanted within the patient. Conventional implantation techniques are used in implanting the lead 14, and its associated medical device, as are known and practiced in the art. See, e.g., Furman et al., *A Practice of Cardiac Pacing*, Chapter 5, pp. 97–127 ("Permanent Pacemaker Implantation"), Futura Publishing Co. (Mt. Kisco, N.Y. 1986).

Where the lead 14 includes a positive fixation distal tip, which is assumed for purposes of the present invention, it is thus evident from FIG. 1, or the above cited reference, that the positive fixation tip not protrude from the lead until such time as the distal tip has been positioned at the desired tissue contact location. Otherwise, the tip could easily snag on the vein wall, or a non-desired tissue location in the heart, thereby causing undesirable tissue damage and/or trauma for the patient.

Referring next to FIG. 2, an enlarged view of the distal end 24 of an implantable lead 14 having an extendable/retractable positive fixation tip is illustrated. The extendable/retractable positive fixation tip in FIG. 2 is shown in its extended position. Portions of the distal end shown in FIG. 2 are cut away for clarity. It is noted that the lead shown in FIG. 2 is a bipolar lead, including both a tip electrode 26 and a ring electrode 28. However, it is to be understood that the present invention is not limited to use with a bipolar lead, as any lead having an extendable/retractable positive fixation tip activated by a stylet could be used with the invention.

The distal end 24 of the lead 14 shown in FIG. 2 includes a screw-in tip 30 as the positive fixation means. This screw-in tip comprises a wire wound in the shape of a helix, ending in a sharp point 32. When extended, as shown in FIG. 2, the screw-in helix tip 30 protrudes out from a hole or opening 33 in the center of the tip electrode 26. When retracted (not shown in FIG. 2), the entire screw-in tip 30 is pulled back inside of the opening 33. A proximal end of the screw-in tip 30 is secured to a carrier member 34 capable of sliding axially within the distal end 24. A biasing spring 36 tends to push the carrier member 34 towards the proximal end of the lead 14 (to the left in FIG. 2), thereby pulling the screw-in tip 30 back inside of the hole 33.

A stylet wire 38, inserted through a lumen 40 of the lead 14, is used to selectively move the screw-in tip 30 from its normally retracted position within the opening 33 to its extended position protruding from the opening 33. As the stylet wire 38 is axially pushed through the lead 14, in the direction of the arrow 39, a tip 42 of the stylet wire eventually contacts the carrier member 34. As the stylet continues to be pushed through the lead 14 in the direction of the arrow 39, the carrier member 34 is likewise pushed axially within the distal end 24, thereby moving the screw-in tip 30 to its extended or protruding position. So long as the stylet 38 remains present within the lead 14, and so long as a sufficient axial force is maintained thereon to hold the carrier member 34 in its distal-most position (to the far right in FIG. 2), then the screw-in tip will remain extended.

Fixation of the screw-in tip 30 is achieved by rotating the screw-in tip clockwise, as viewed from the proximal end of the lead, a prescribed number of turns. Advantageously, for the embodiment shown in FIG. 2, the carrier member 34 is keyed or otherwise prevented from rotating relative to the distal electrode 26 and the body of the lead 14. Hence, rotation of the lead 14 in a clockwise direction (as viewed from the proximal end of the lead) also causes the screw-in tip to rotate. As it rotates, the sharp tip 32 engages body tissue and screws itself therein, thereby positively holding the distal electrode 26 against the body tissue at the fixation site.

FIG. 3 shows a plan view of the bipolar implantable lead 14 having an extendable/retractable positive fixation tip 24 in its extended position. Also shown in FIG. 3 are some representative dimensions for the lead 14. These dimensions are not meant to be limiting, but are shown merely to illustrate a preferred lead 14 that may be used with the implant tool of the present invention.

In the preferred embodiment, the length of the lead 14 may be 52 or 56 cm in length, depending upon the size of the patient. The distal electrode 26 is, preferably, spaced apart from the ring electrode 28 about 12.5 mm. The screw-in tip 30, in its extended position, protrudes out from the distal electrode 26 about 1.8 mm. The size (diameter at 45) of the lead is roughly 6.8 FR (French). A suture sleeve 42, including two eyelets 43, slidably passes over the body of the lead 14 and provides a convenient means for the implanting physician to anchor the lead body within the patient after the distal tip has been properly positioned and secured.

A proximal end 44 of the lead 14 includes a standard 3.2 mm VS-1 connector. Such a connector is well defined in the literature, see, e.g., Calfee et al., "A Voluntary Standard for 3.2 mm Unipolar and Bipolar Pacemaker Leads and Connectors," PACE, Vol. 9, pp. 1181-85 (Nov.-Dec. 1986). The VS-1 connector includes a hollow connector pin 46 that is electrically connected to the distal electrode 26. A proximal ring electrode 48, if used, is similarly electrically connected to the distal ring electrode 28. (Note that the proximal and distal ring electrodes 48 and 28 are only used for a bipolar lead.) A lumen (or bore) 40 passes all the way through the lead 14, beginning at the connector pin 46 and terminating at the carrier member 34 at the distal end 24.

FIG. 4 shows an implant fixation tool 50 and a stylet 52 made in accordance with the present invention. The implant tool 50 includes a cylindrical housing having a body portion 54 and an end portion 56. The end portion 56 is rotatable relative to the body portion 54. A hole or opening 58 in the end portion 56 is sized to receive the connector pin 46. The body portion 54 includes a longitudinal slot 60, best seen in FIGS. 9 and 10, that begins at a proximal end of the implant tool 50 and continues for about ¼ of the length of the implant tool 50. Near the proximal end of this slot 60 is a first recess 62. This first recess 62 may be labeled RETRACT. At or near the distal end of this slot 60 is a second recess 64. This second recess 64 may be labeled EXTEND.

Still referring to FIG. 4, the stylet 52 includes a length of stylet wire 38. The proximal end of the stylet wire 38 is attached to a knob 66. The knob 66 has an elongate rod-shaped body 67 that has a stub pin 68 at its distal end, and a gripping handle 70 around its proximal end. The stub pin protrudes out from the knob body 67 in a substantially transverse direction relative to a longitudinal axis of the knob.

An opening 72 at the proximal end of the implant tool 50 is sized to receive the knob body portion 67 of the stylet knob 66. The stub pin 68 is sized to be slidably received within the slot 60. Further, the recesses 62 and 64 are sized to receive the stub pin 68 by way of an interference fit. That is, at the point where each recess 62 or 64 connects with the slot 60, each recess includes a narrow neck portion that has a width adapted for an interference fit with the width of the stub pin. After this narrow neck portion, the recesses open up to a wider width.

Figure 8:
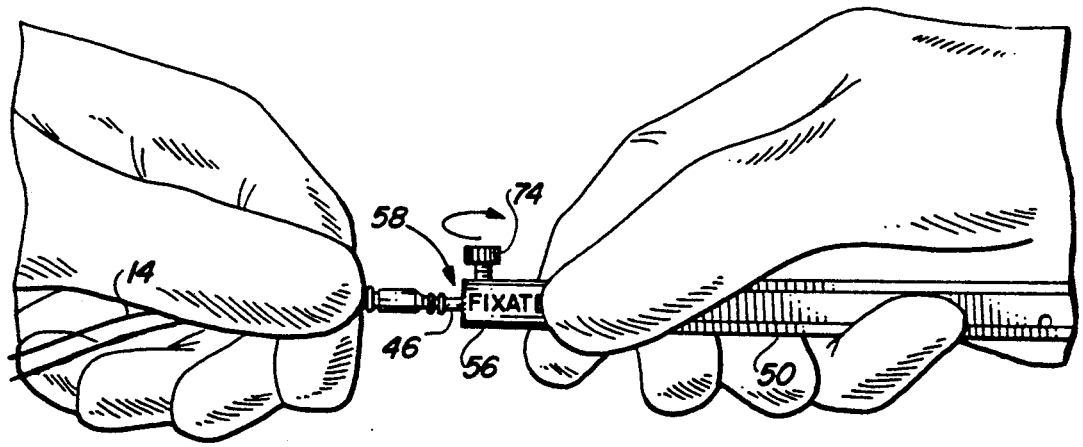
FIG. 8 depicts the manner of attaching a proximal end of the lead of FIG. 3 to the fixation tool of FIG. 4.

In order to use the implant tool 50, the connector pin 46 of the lead 14 is inserted into the hole 58 at the distal end of the implant tool 50. A thumb-screw or set screw 74, having a large head that enables it to be easy tightened or loosened using one's thumb and fingers, provides a convenient means for detachably securing the connector pin to the implant tool 50, as shown in FIG. 5 and FIG. 8. The stylet wire 38 is inserted through the implant tool, from proximal end to distal end, and into the lumen 40 of the lead 14. Advantageously, the portion of the lumen 40 that passes through the connector pin 46 includes an inner bevel at its proximal end that guides the stylet tip 42 into the lumen, just like a funnel guides liquid into a narrow opening.

As the knob body 67 enters the hole 72 at the proximal end of the tool 50, the stylet 52 is twisted or rotated, as required in order to align the stub pin 68 with the slot 60. The stylet 52 is then further inserted into the tool 50 until the stub pin 68 is adjacent a desired recess 62 or 64. Then, the stylet 52 is again twisted, using the stylet knob 66, rotating the stub pin 68 into the desired recess through the interference fit. This action effectively locks the stylet 52 in the desired position relative to the tool 50 and the lead 14 (which is detachably secured to the tool 50).

The length of the stylet wire 38 is carefully selected in combination with the length of the lead 14 in order to assure that when the stub pin 68 is placed in the recess 62, the tip 42 of the stylet wire 38 has not yet engaged the screw-in tip carrier member 34 within the distal end of the lead 14. Thus, the screw-in tip 30 remains in its retracted position so long as the stub pin 68 remains within the recess 62. When the stub pin 68 is placed in the recess 64, however, the tip 42 of the stylet wire 38 has advanced sufficiently far within the lumen 40 of the lead 14 to engage the carrier member 34 and push it to its distal-most position (to the right, as shown in FIG. 2). Hence, the screw-in tip 30 is extended and protrudes from the distal end of the lead 14 for so long as the stub pin 68 remains within the recess 64. Because the stub pin 68 can effectively be locked within the recess 62 or the recess 64, due to the interference fit between the stub pin and the neck of the recess, the tip of the stylet wire 38 can thus be maintained at the proper position within the lead 14 to assure that the screw-in tip 30 is either fully retracted or fully extended.

Thus, as shown in FIG. 5, when the stub pin 68 is placed within the recess 64, which is the recess closest to the distal tip of the tool 50, the tip 42 of the stylet wire 38 has advanced sufficiently far to fully extend the screw-in tip 30. In the preferred embodiment, the length of the stylet wire 38, from the distal end of the rod 66 to its distal tip 42 is about 6 cm longer than the length of the lead 14 with which the implant tool 50 and stylet 52 are used. This additional length accounts for the length added to the lead by attaching the implant tool 50 thereto. The axial spacing between the recess 62 and the recess 64, in the preferred embodiment is about 2 cm. The longitudinal length of the slot 60 is about 2.6 cm, and the overall length of the implant tool 50 is about 10 cm. The length of the knob 66 of the stylet 52 is about 4.3 cm, including the gripping portion 70. The diameter of the stub pin 68 is about 1.5 mm, and the width of the slot 60 is about 1.6 mm. The stub pin 68 protrudes out from the surface of the elongate knob body 67 of the stylet knob 66 about 2 mm. It is to be emphasized that these dimensions are only exemplary and not limiting. Both the implant tool 50 and the stylet knob 66 may be made from Acrylonitrile-Butadiene-Styrene (ABS) or an ABS-type plastic which has the properties of being sterilizable, usable with a solvent, and has good dimensional stability, using conventional molding and machining techniques.

Thus, in summary, the implant tool 50 fits on the connector pin 46 of the implantable lead 14 and is held in place by tightening the thumb-screw 74 at the distal end of the tool 50. The knob 66 at the proximal end of the customized stylet 52 includes a rod-shaped plastic body 67 that includes the stub pin 68 near its distal end. The stub pin 68 serves the function of a locator tab that fits into the slot 60 in the proximal end of the implant tool 50 and allows the stylet to be locked in either the helix-extended or helix-retracted position, where the term "helix" refers to the screw-in tip.

Referring next to FIG. 6, there is illustrated one manner of inserting the stylet of FIG. 4 through the fixation implant tool 50 and implantable lead 14. Basically, this method involves grasping the implant tool 50 in one hand, e.g., the left hand, after the tool has been attached to the connector pin 46 of the lead 14 (see FIG. 8, below). The stylet wire 38 is then grasped between the fingers of the other hand, e.g., the right hand, and pushed through the tool 50 into the lumen 40 of the lead.

If one or more tight bends are induced in the lead 14 as a result of its placement in the patient's vascular system, additional force may be required to advance the stylet wire 38 (especially a J-shaped stylet wire) through the lead body. When this force is applied to the stylet wire 38 near the end of the fixation tool 50, the stylet wire 38 may have a tendency to bow up through the slot 60 at the proximal end of the tool 50. If enough force is applied to the stylet wire 38, it may become kinked, making advancement thereof even more difficult.

To prevent such bowing and possible kinking, the user's thumb of the hand holding the implant tool 50 should be placed over the slot 60 while advancing the stylet wire 38 with the other hand, as shown in FIG. 6. Also, moving the body of the pacing lead 10 backward and forward slightly while advancing the stylet wire 38 therethrough may also reduce the stylet insertion force.

Figure 7:
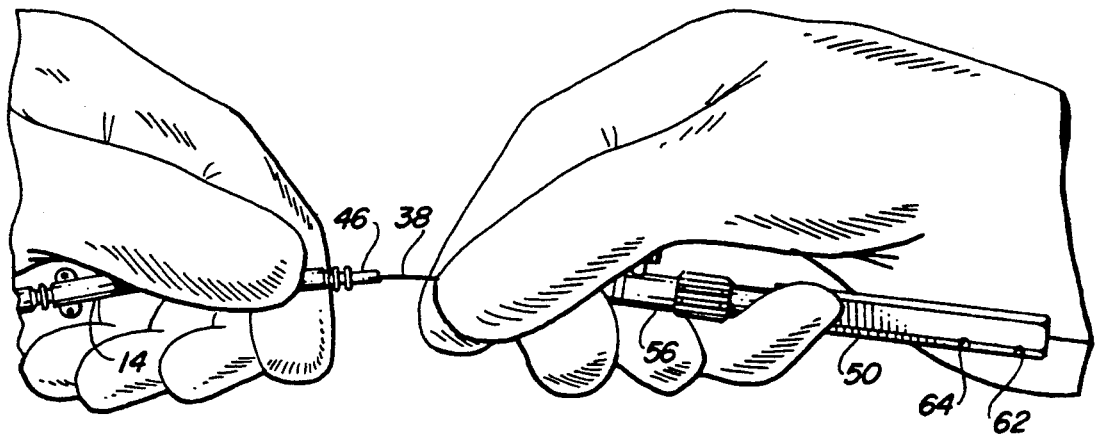

In those rare instances where advancement of the stylet wire 38 through the lead 14 is still difficult, it may be necessary to loosen the thumb-screw 74 and detach the connector pin 46 of the lead 14 from the fixation implant tool 50. The stylet wire 38 may then be advanced by grasping and pushing the stylet wire 38 just beyond the point where it enters the connector pin 46, as illustrated in FIG. 7. Once the stylet wire 38 is fully advanced, the tool 50 may then be reattached to the connector pin 46 of the lead 14 and the stylet stub pin 68 may be inserted into the extend recess 64 of the tool 50 in order to extend the helix screw-in tip 30 for proper fixation.

FIG. 8 depicts the manner of attaching the connector pin 46 at the proximal end of the lead 14 to the distal end of the fixation tool 50. Essentially, after the lead 14 has been implanted in the patient's vascular system, the lead 14 is grasped in one hand while holding the implant tool 50 in the other hand. The thumb-screw 74 is rotated counterclockwise a few turns to assure that the opening 58 in the end of the tool 50 is open a sufficient amount the allow the connector pin 46 to be inserted therein. The connector pin 46 is then inserted into the opening 58, and the thumb-screw 74 is turned clockwise a sufficient distance to lock the connector pin 46 to the implant tool 50.

FIG. 9 shows the implant tool 50 with the lead 14 attached thereto and with the stylet 52 locked in a "retract" position. In this position, the stub pin 68 of the stylet 52 has been inserted through the slot 60 so as to be locked in the recess 62 (RETRACT position) on the side of the tool 50. This action causes the screw-in helix tip 30 to remain retracted within the opening 33 of the distal electrode 26 of lead 114, as shown in FIG. 9A.

FIG. 10 shows the implant tool 50 with the lead 14 attached thereto and with the stylet 52 locked in an "extend" position. In this position, the stub pin 68 of the stylet 52 has been inserted through the slot 60 sufficiently far so as to be locked in the recess 64 (EXTEND position) on the side of the tool 50. This action causes the screw-in helix tip 30 to protrude from the opening 33 of the distal electrode 26 of lead 14, as shown in FIG. 10A.

With the screw-in helix tip 30 locked in its extend position, as shown in FIG. 10, the lead 14 is rotated a prescribed number of turns in order to positively attach the tip to the body tissue. Advantageously, this rotating of the lead can be done using one hand as illustrated in FIG. 11. The body portion 54 of the implant tool 50 is held in the user's hand, e.g., the right hand. The rotatable end portion 56 of the implant tool 50 is grasped between the thumb and forefinger of the hand and rotated clockwise, as viewed from the proximal end. To facilitate this rotation, several ribs 57 are included around the periphery of the rotatable end portion 56. For the preferred lead shown in FIG. 3, it is recommended that four complete rotations of the lead be used for fixation in the ventricle, and six complete rotations be used for fixation in the atrium. To successfully transfer torque to the distal tip of the lead, it is also recommended that the lead body be gently advanced and withdrawn one or two centimeters as the implant tool is rotated.

After the lead tip 30 is believed to be secure, the stylet 52 is withdrawn within the implant tool 50 to the retract position. The position of the electrode 26 may then be confirmed using conventional fluoroscopy techniques.

Once the position of the electrode 26 has been confirmed, the tool 50 and the stylet 52 are removed from the lead, and the lead is then connected to the appropriate test equipment or medical device for electrical testing and/or operation.

As described above, it is thus seen that the present invention provides an implant tool, and method of using the same, that greatly facilitates the fixation of a extendable/retractable positive fixation tip to body tissue. This it does by providing an implant tool and method of use that selectively yet positively locks a customized stylet in one of two positions relative to the lead, a first position that keeps the positive fixation tip in a retracted position; and a second position that forces the positive fixation tip to its extended position. Advantageously, a visual indication is provided at the implant tool as to which of the two positions—fixation tip extended or retracted—the stylet is locked. Further, the implant tool of the present invention may be conveniently held in one hand while rotating the lead using the thumb and fingers of the same hand. This one-handed rotation renders the positive fixation of the extended screw-in helix tip into body tissue a relatively simple task.

While the invention herein disclosed has been described by means of specific embodiments and applications thereof, numerous modifications and variations could be made thereto by those skilled in the art without departing from the scope of the invention set forth in the claims.

What is claimed is:

1. An apparatus for implanting an implantable lead comprising:
   (a) an implantable lead having a lead body intermediate a proximal end and a distal end, said lead body having a connector pin at its proximal end, said connector pin and lead body having a lumen through the center thereof through which a stylet may be inserted, said lead body having an extendable/retractable positive fixation tip, said positive fixation tip including a screw-in helix tip, a housing means for surrounding said screw-in helix tip, and biasing means for axially biasing said screw-in helix tip towards the proximal end of said lead so that said screw-in helix tip is retracted within said housing means;
   (b) a stylet having a distal tip and a proximal end, said stylet including a length of a relatively stiff wire, the distal tip of said stylet being adapted to engage said biasing means and push said screw-in helix tip towards an extended position beyond said housing means, said stylet having a transverse tab on the proximal end of said stylet;

(c) an implant tool having means for selectively holding said stylet within the lumen of said lead in a first or second predetermined holding position, said implant tool including:

a hollow cylindrical housing having an inner diameter that allows said stylet to be inserted into a proximal end of said housing and longitudinally guided therethrough to the lumen of said connector pin and lead, whereby said stylet may be inserted through said housing into said lead;

locking means for detachably locking the connector pin of said lead to a distal end of said housing;

first seating means within said housing into which said transverse tab on the proximal end of said stylet may be selectively seated as said stylet is inserted through said housing; and second seating means within said housing into which said transverse tab on the proximal end of said stylet may be selectively seated, said second seating means being a predetermined distance closer to the distal end of said housing than said first seating means;

said first and second seating means being positioned within said housing so that the distal tip of said stylet does not engage said biasing means when the transverse tab is seated in said first seating means so that said screw-in helix tip assumes a retracted position, but does engage said biasing means and extend said screw-in helix tip beyond said housing means when the transverse tab is seated in said second seating means.

2. The lead implanting apparatus, as set forth in claim 1, further including visual indicator means on said cylindrical housing for providing a visual indication of whether said stylet is being held in said first or second seating means.

3. The lead implanting apparatus, as set forth in claim 1, wherein:

the transverse tab includes a stub pin near the proximal end of said stylet, said stub pin comprising a radial protrusion that extends out from said stylet a small distance;

the housing includes:

a longitudinal slot along one side of said housing, beginning at the proximal end of said housing, and continuing a prescribed distance towards the distal end of said housing, said slot and said stub pin each having a width such that the width of said slot is slightly wider than the width of said stub pin, whereby said stub pin may freely slide within said longitudinal slot as said stylet is advanced or retracted within the lumen of said lead;

a first recess having an opening which leads to said longitudinal slot for selectively receiving said stub pin when said stub pin is adjacent said first recess and said stylet is rotated so as to place said stub pin within said first recess; and a second recess having an opening which leads to said longitudinal slot for selectively receiving said stub pin when said stub pin is adjacent said second recess and said stylet is rotated so as to place said stub pin within said second recess, said second recess being closer to the distal end of said housing than is said first recess, whereby said first predetermined holding position may be selectively engaged by placing the stub pin in said first recess, and said second predetermined holding position may be selectively engaged by placing the stub pin in said second recess.

4. The lead implanting apparatus, as set forth in claim 3, wherein said first and second recesses include means for lockably holding said stub pin within a selected one of said first or second recesses.

5. The lead implanting apparatus, as set forth in claim 4, wherein said means for lockably holding said stub pin in said recesses comprises a narrow neck at the respective opening of said first and second recess, said narrow neck and said stub pin each having a width such that the width of said narrow neck interferingly fits with the width of said stub pin.

6. The lead implanting apparatus, as set forth in claim 3, wherein said stylet further includes a stylet knob at the proximal end thereof firmly secured to said stylet wire, rotation of said stylet knob causing said stub pin to rotate.

7. The lead implanting apparatus, as set forth in claim 6, wherein said knob includes:

an elongate rod having a longitudinal axis and proximal and distal ends;

said stylet wire being substantially coaxial with the longitudinal axis of said rod and attached to a distal end thereof;

gripping means attached around a periphery of said rod near the proximal end thereof; and said stub pin protruding out from the periphery of said rod near the distal end thereof.

8. The lead implanting apparatus, as set forth in claim 1, wherein said screw-in helix tip is secured to said lead body such that rotation of said lead body rotates said screw-in helix tip, and wherein said implant tool further includes means for rotating said lead body as a unit, whereby when said screw-in helix tip is in the extended position and positioned adjacent to body tissue, and when said lead body is rotated by said rotating means, said screw-in helix tip will positively engage body tissue.

9. The leading implanting apparatus, as set forth in claim 8, wherein said means for rotating said lead body includes an end portion of said housing that is rotatable about a longitudinal axis of said housing relative to a body portion, said end portion including the distal end to which said connector pin is detachably connected, said body portion being holdable within one hand, and said end portion being grippable between the thumb and first finger of the hand and rotatable using the thumb and first finger.

10. The lead implanting apparatus, as set forth in claim 8, wherein:

the means for rotating said lead body includes an end portion of said housing that is rotatable about a longitudinal axis of said housing relative to a body portion and the stylet;

the body portion includes the longitudinal slot and the first and second recesses, said stylet being seated in either the first or second recess;

the end portion includes the distal end to which said connector is detachably connected by said locking means;

whereby when the connector pin of the lead is connected to the locking means on the end portion and the stylet is seated in the second recess and the end portion is rotated, the lead is rotated relative to the stylet.

11. A method of implanting an endocardial lead having an extendable/retractable screw-in helix tip, said endocardial lead having a proximal connector pin adapted for being connected to an implantable pacemaker, said connector pin and endocardial lead having a lumen through the center thereof through which a stylet may be inserted, said endocardial lead including biasing means at its distal tip for tending to pull the extendable-retractable screw-in helix tip into a retracted position, said helix tip being coupled to said lead such that rotation of said lead rotates said helix tip, said method comprising the steps of:

(a) detachably connecting the proximal connector pin of said lead to a first end of a hollow implant tool, said first end being rotatable relative to a body of said implant tool;

(b) inserting said stylet through said implant tool and into the lumen of said lead a first prescribed distance so that a stub pin located on a proximal end of said stylet enters a first recess within the body of said implant tool, said first prescribed distance being such that a tip of said stylet has not advanced sufficiently far within said lead to push said screw-in helix tip to an extended position;

(c) holding said stylet within said implant tool and said lead at said first prescribed distance while transvenously inserting said screw-in helix tip of said lead into a desired implant location;

(d) advancing said stylet through said implant tool and said lead a second prescribed distance so that said stub pin located on a proximal end of said stylet enters a second recess within the body of said implant tool, said second prescribed distance being such that a tip of said stylet has advanced sufficiently far within said lead to push said screw-in helix tip to its extended position; and (e) holding said stylet within said implant tool and said lead at said second prescribed distance while rotating said screw-in first end of said implant tool relative to the body of said implant tool, whereby said screw-in helix tip rotates and is positively secured to body tissue at said desired implant location.

12. Apparatus for implanting an implantable lead comprising:

an implantable lead having a lead body intermediate a proximal end and a distal end, said lead body having a connector pin at its proximal end, said connector pin and lead body having a lumen through the center thereof through which a stylet may be inserted, said lead body having an extendable/retractable positive fixation tip, said positive fixation tip including a screw-in helix tip, a housing means for surrounding said screw-in helix tip, and biasing means for axially biasing said screw-in helix tip towards the proximal end of said lead so that said screw-in helix tip is retracted within said housing means;

a stylet having a distal tip and a proximal end, said stylet including a length of a relatively stiff wire that is adapted to be inserted through said lumen to guide said lead during implantation, the distal tip of said stylet being adapted to engage said biasing means and push said screw-in helix tip towards an extended position beyond said housing means, from which extended position said screw-in helix tip may be positively engaged with body tissue; and an implant tool having positioning means for selectively positioning said stylet within the lumen of said lead in either a first or a second predetermined position corresponding to a fully retracted and a fully extended position, respectively, for said screw-in helix tip, said positioning means including:

first locking means for locking said stylet in said first predetermined position, said first locking means maintaining the distal tip of said stylet short of engagement with said biasing means;

means for guiding the movement of said stylet a predetermined distance between said first position and said second position; and second locking means, separated from the first locking means by a predetermined distance, for locking said stylet in said second predetermined position, said second locking means maintaining the distal tip of said stylet in engagement with said biasing means so as to force said screw-in helix tip to be fully extended beyond said housing means.

* * * * *